(12) United States Patent
Carson et al.

(10) Patent No.: US 7,211,599 B2
(45) Date of Patent: May 1, 2007

(54) USE OF ETODOLAC TO TREAT HYPERPLASIA

(75) Inventors: Dennis A. Carson, La Jolla, CA (US); Lorenzo M. Leoni, San Diego, CA (US); Mary Patricia Corr, San Diego, CA (US)

(73) Assignees: The Regents of the University of California, Oakland, CA (US); Cephalon, Inc., Frazer, PA (US)

( * ) Notice: Subject to any disclaimer, the term of this patent is extended or adjusted under 35 U.S.C. 154(b) by 36 days.

(21) Appl. No.: 10/667,208

(22) Filed: Sep. 19, 2003

(65) Prior Publication Data

US 2004/0127431 A1 Jul. 1, 2004

Related U.S. Application Data

(60) Provisional application No. 60/412,193, filed on Sep. 19, 2002.

(51) Int. Cl.
| | |
|---|---|
| A61K 31/40 | (2006.01) |
| A61K 31/56 | (2006.01) |
| A61K 31/50 | (2006.01) |
| A61K 31/18 | (2006.01) |
| A61K 31/12 | (2006.01) |

(52) U.S. Cl. .................. 514/411; 514/171; 514/249; 514/603; 514/678

(58) Field of Classification Search ............. 514/411, 514/171, 249, 603, 678
See application file for complete search history.

(56) References Cited

U.S. PATENT DOCUMENTS

| | | | |
|---|---|---|---|
| 3,053,255 A | 9/1962 | Meyer | |
| 3,710,795 A | 1/1973 | Higuchi et al. | |
| 3,843,480 A | 10/1974 | Dreher | |
| 3,843,681 A | 10/1974 | Demerson et al. | .. 260/326.14 R |
| 3,939,178 A | 2/1976 | Demerson et al. | |
| 3,948,254 A | 4/1976 | Zaffaroni | |
| 3,948,262 A | 4/1976 | Zaffaroni | |
| 3,974,179 A | 8/1976 | Demerson et al. | |
| 3,993,073 A | 11/1976 | Zaffaroni | |

(Continued)

FOREIGN PATENT DOCUMENTS

| | | |
|---|---|---|
| CA | 1299577 | 4/1992 |
| DE | 2226340 | 3/1973 |
| EP | 0289262 | 11/1986 |
| GB | 1436893 | 5/1976 |
| WO | WO-96/28148 | 9/1996 |
| WO | WO-9748391 A3 | 12/1997 |
| WO | WO-98/09603 | 3/1998 |
| WO | WO-98/18490 | 5/1998 |
| WO | WO-98/40078 A1 | 9/1998 |
| WO | WO-00/02555 | 1/2000 |
| WO | WO-00/13410 | 3/2000 |
| WO | WO-0106990 A2 | 2/2001 |
| WO | WO-02/02125 A1 | 1/2002 |
| WO | WO-0212188 A2 | 2/2002 |

OTHER PUBLICATIONS

Abramson, S. B., et al.; "The Mechanisms of Action of Nonsteroidal Antiimflammatory Drugs", *Arthritis & Rheumatism*, 32 (1), (Jan. 1989), 1–9.

Alexanian, R., et al., "The Treatment of Multiple Myeloma", *The New England Journal of Medicine*, 330 (7), (Feb. 17, 1994), 484–489.

(Continued)

*Primary Examiner*—Ardin H. Marschel
*Assistant Examiner*—Amy Lewis
(74) *Attorney, Agent, or Firm*—Schwegman, Lundberg, Woessner & Kluth P.A.

(57) ABSTRACT

The present invention provides a therapeutic method to treat non-malignant diseases characterized by the excessive tissue growth, e.g., hyperplastic diseases, comprising administering to a mammal (e.g., human) afflicted with excessive tissue growth, an effective amount of a derivative of an indole compound of formula (I):formula (I):

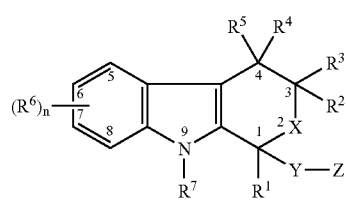

wherein $R^1$ is lower alkyl, (hydroxy)lower alkyl, lower alkenyl, lower alkynyl, lower cycloalkyl, phenyl, benzyl or 2-thienyl; $R^2$, $R^3$, $R^4$ and $R^5$ are the same or different and are each hydrogen or lower alkyl; each $R^6$ is individually hydrogen, lower alkyl, hydroxy, (hydroxy)lower alkyl, lower alkoxy, benzyloxy, lower alkanoyloxy, nitro or halo, $R^7$ is hydrogen, lower alkyl or lower alkenyl, X is oxy and thio, Y is carbonyl, $—(CH_2)_{1-3}—$, $—(C_1–C_3)\text{alkyl}(CO)—$, or $—(CH_2)_{1-3}SO_2—$; Z is hydroxy, lower alkoxy, $(C_2–C_4)$ acyloxy, $—N(R^8)(R^9)$, phenylamino, (ω-(4-pyridyl)($C_2–C_4$ alkoxy), (ω-(($R^8$)($R^9$)amino)($C_2–C_4$ alkoxy), an amino acid ester of (ω-(HO)($C_2–C_4$))alkoxy, $—N(R^8)CH(R^8)CO_2H$, 1'-D-glucuronyloxy, $—SO_3H$, $—PO_4H_2$, $—N(NO)(OH)$, $—SO_2NH_2$, $—PO(OH)(NH_2)$, $—OCH_2CH_2N(CH_3)_3^+$, or tetrazolyl; wherein $R^8$ and $R^9$ are each H, $(C_1–C_3)$alkyl or together with N are a 5- or 6-membered heterocyclic ring comprising 1–3 $N(R^8)$, S or nonperoxide O; n is 0, 1, 2, or 3; wherein $R^8$ and $R^9$ are each H, $(C_1–C_3)$alkyl or together with N are a 5- or 6-membered heterocyclic ring comprising 1–3 $N(R^8)$, S or nonperoxide O; each alkyl or phenyl group of $R^1$, $R^2$, $R^3$, $R^4$, $R^5$, $R^6$, $R^7$ and Z is optionally substituted with 1, 2, or 3 $(C_1–C_4)$alkyl groups; or a pharmaceutically acceptable salt thereof.

11 Claims, No Drawings

U.S. PATENT DOCUMENTS

| | | | |
|---|---|---|---|
| 4,041,169 A | 8/1977 | Demerson et al. | |
| 4,179,503 A | 12/1979 | Asselin et al. | |
| 4,310,509 A | 1/1982 | Berglund et al. | |
| 4,337,760 A | 7/1982 | Rubin | 128/1 R |
| 4,460,562 A | 7/1984 | Keith et al. | |
| 4,466,953 A | 8/1984 | Keith et al. | |
| 4,482,534 A | 11/1984 | Blank | |
| 4,485,097 A | 11/1984 | Bell | |
| 4,505,891 A | 3/1985 | Ito | |
| 4,533,540 A | 8/1985 | Blank | |
| 4,542,012 A | 9/1985 | Dell | |
| 4,542,013 A | 9/1985 | Keith | |
| 4,560,555 A | 12/1985 | Snider | |
| 4,585,877 A | 4/1986 | Demerson et al. | |
| 4,597,961 A | 7/1986 | Etscorn | |
| 4,608,249 A | 8/1986 | Otsuka et al. | |
| 4,686,213 A | 8/1987 | Ferdinandi et al. | |
| 4,748,252 A | 5/1988 | Ferdinandi et al. | |
| 4,806,356 A | 2/1989 | Shaw | |
| 4,940,587 A | 7/1990 | Jenkins et al. | |
| 5,561,151 A | 10/1996 | Young et al. | 514/411 |
| 5,599,946 A | 2/1997 | Vincenzo et al. | |
| 5,776,967 A | 7/1998 | Kreft et al. | |
| 5,780,435 A | 7/1998 | Garnick et al. | |
| 5,811,558 A | 9/1998 | Adger et al. | 548/427 |
| 5,824,699 A | 10/1998 | Kreft et al. | |
| 5,939,455 A | 8/1999 | Rephaeli | 514/547 |
| 5,955,504 A | 9/1999 | Wechter et al. | 514/568 |
| 5,968,974 A | 10/1999 | Kargman et al. | |
| 6,066,741 A | 5/2000 | Vigano' et al. | 548/432 |
| 6,110,955 A | 8/2000 | Nudelman et al. | |
| 6,160,018 A | 12/2000 | Wechter et al. | |
| 6,300,313 B1 | 10/2001 | Engel et al. | |
| 6,545,034 B1 | 4/2003 | Carson et al. | 514/411 |
| 6,552,055 B1 | 4/2003 | Spiegelman et al. | |
| 2003/0004142 A1 * | 1/2003 | Prior et al. | 514/165 |
| 2003/0004143 A1 * | 1/2003 | Prior et al. | 514/165 |
| 2005/0239752 A1 | 10/2005 | Carson et al. | |

OTHER PUBLICATIONS

Barlogie, B., et al., "Prognostic Factors with High–Dose Melphalan for Refractory Multiple Myeloma.", Blood, 72, (1988), 2015–2019.

Bataille, R., et al., "Multiple Myeloma", New England Journal of Medicine, 336, (1997), 1657–1664.

Becker–Scharfenkamp, U., et al., "Evaluation of the Stereoselective Metabolism of the Chiral Analgesic Drug Etodolac by High–Performance Liquid Chromatography", Journal of Chromatography, 621 (2), (Nov. 24, 1993), 199–207.

Bellosilo, B., "Aspirin and Salicylate Induce Apoptosis and Activation of Caspases in B–Cell Chronic Lymphocytic Leukemia Cells", Blood, 92 (4), (Aug. 15, 1998), 1406–1414.

Berendes, U., et al., "Simultaneous Determination of the Phase II Metabolites of the Non Steriodal Anti–inflammatory Drug Etodolac in Human Urine", Enantiomer, 1, Abstract Only, Chemical Abstracts, Abstract No. 126:207064q,(1996), 415–422.

Brenna, E., et al., "New Enzymatic and Chemical Approaches to Enantiopure Etodolac", Tetrahedron, 53, 17769–17780.

Brocks, D. R., et al., "Etodolac Clinical Pharmacokinetics", Clinical Pharmacokinetics, 26, (4), (1994), 259–274.

Carson, D. A., et al., "Oral Antilymphocyte Activity and Induction of Apoptosis by 2–chloro–2'–arabino–fluoro–2'–deoxyadenosine", Proc. Natl. Acad. Sci. USA, 89 (7), (Apr. 1992), 2970–2974.

Chinetti, G., et al., "Activation of Proliferator–activated Receptors alpha and Y Induces Apoptosis of Human Monocyte–derived Macrophages", The Journal of Biological Chemistry, 273 (40), (Oct 2, 1998), 25573–25580.

Cunningham, D. et al., "High–dose Melphalan for Multiple Myeloma: Long–term Follow–up Data", Journal of Clinical Oncology, 12, (1994), 764–768.

Demerson, C. A., et al., "Etodolic Acid and Related Compounds. Chemistry and Antiinflammatory Actions of Some Potent Di– and Trisubstituted 1,3,4,9–Tetrahydropyrano[3,4–b]indole–1–acetic Acids", Journal of Medicinal Chemistry, 19 (3), (1976), 391–395.

Demerson, C. A., et al., "Resolution of Etodolac and Antiinflammatory and Prostaglandin Synthetase Inhibiting Properties of the Enantiomers", J. Med. Chem., 26 (12), (Dec. 1983), 1778–1780.

Drachenberg, D. F., et al., "Treatment of Prostate Cancer: Watchful Waiting, Radical Prostatectomy, and Cryoablation", Seminars in Surgical Oncology, 18 (1), (Jan./Feb. 2000), 37–44.

Duffy, C. P., et al., "Enhancement of Chemotherapeutic Drug Toxicity to Human Tumour Cells In Vitro by a Subset of Non–Steroidal Anti–Inflammatory Drugs (NSAIDs)", European Journal of Cancer, 34 (8), (Jul. 1998), 1250–1259.

Hahnfeld, L. E., et al., "Prostate Cancer", The Medical Clinics of North America—The Aging Male Patient, 83 (5), (Sep. 1999), 1231–1245.

Harousseau, J. L., et al., "Double–Intensive Therapy in High–Risk Multiple Myeloma", Blood, 79 (11), (Jun. 1, 1992), 2827–2833.

Krajewski, S., et al., "Detection of Multiple Antigens on Western Blots", Analytical Biochemistry, 236 (2), Article No. 0160,(May 1996), 221–228.

Landis, S. H., et al., "Cancer Statistics, 1998", CA Cancer J. Clin., 48 (1), (1998), 6–29.

Lee, D. H., et al., "Proteasome Inhibitors: Valuable New Tools For Cell Biologists", Trends in Cell Biology, 8, (Oct. 1998), 397–403.

Lehmann, J. M., et al., "Peroxisome Proliferator–activated Receptors alpha and Y Are Activated by Indomethacin and Other Non–steroidal Anti–inflammatory Drugs", The Journal of Biological Chemistry, 272 (6), (Feb. 7, 1997), 3406–3410.

Leman, Eddy S., et al., "Characterization of the Nuclear Matrix Proteins in a Transgenic Mouse Model for Prostate Cancer", Journal of Cellular Biochemistry, 86, (2002), 203–212.

Leoni, L. M., et al., "Induction of an Apoptotic Program in Cell–Free Extracts by 2–Chloro–2'–deoxyadenosine 5'–triphosphate and Cytochrome C", PNAS, USA, 95 (16), (Aug. 4, 1998), 9567–9571.

Lochmuller, C. H., et al., "Chromatographic Resolution of Enantiomers—Selective Review", Journal of Chromatography, 113 (3), (Oct. 22, 1975), 283–302.

Martel, R. R., et al., "Anti–inflammatory and Analgesic Properties of Etodolic Acid in Rats", Canadian Journal of Physiology and Pharmacology, 54 (3), (Jun. 1976), 245–248.

Mooney, P. T., et al., "Cell Pathways' Exisulind 'Aptosyn' Demonstrates Potential to Delay Hormone Therapy in Post-Prostatectomy Men at Risk of Prostate Cancer Recurrence", http://biz.yahoo.com/bw/000501/ga_cell_pa_1.html, (May 2000), 3 pages.

Nardella, Francis A., et al., "Enhanced Clearance of Leukemic Lymphocytes in b Cell Chronic Lymphocytic Leukemia (CLL) with Etodolac", *Arthritis & Rheumatism*, 42 (9) *Supplement, Abstract No.* 41, (Sep. 1999), p. S56.

Ricote, M., et al., "The Peroxisome Proliferator–Activated Receptor–Y is a Negative Regulator of Macrophage Activation", *Nature*, 391, (Jan. 1, 1998), 79–82.

Riedel, D. A., et al., "The Epidemiology of Multiple Myeloma", *Hematology/Oncology Clinics of North America, Multiple Myeloma*, 6 (2), (Apr. 1992), 225–247.

Royall, J. A., et al., "Evaluation of 2',7'–Dichlorofluorescin and Dihydrorhodamine 123 as Fluorescent Probes for Intracellular H2O2 in Cultured Endothelial Cells", *Archives of Biochemistry and Biophysics*, 302 (2), (May 1, 1993), 348–355.

Shiff, S. J., et al., "Nonsteroidal Antiinflammatory Drugs Inhibit the Proliferation of Colon Adenocarcinoma Cells: Effects on Cell Cycle and Apoptosis", *Experimental Cell Research*, 222, Article No. 0023,(1996), 179–188.

Tang, D. G., et al., "Target to Apoptosis: A Hopeful Weapon for Prostate Cancer", *The Prostate*, (1997), 284–293.

Van Breemen, R. B., et al., "Characterization of Oxygen–Linked Glucuronides by Laser Desorption Mass Spectrometry", *Biomed. Mass Spectrom.*, 11, Abstract Only, Chemical Abstracts, Abstract No. 101:106777c,(1984), 278–283.

Venuti, M. C., et al., "Synthesis and Biological Evaluation of omega–(N,N,N–trialkylammonium)alkyl Esters and Thioesters of Carboxylic Acid Nonsteroidal Antiinflammatory Agents", *Pharm. Res.*, 6, Abstract Only, Chemical Abstracts, Abstract No. 112:111681y,(1989), 867–873.

Wang, X., et al., "Antipoptotic Action of 1,25–Dihydroxyvitamin D3 is Associated with Increased Mitochondrial MCL–1 and RAF–1 Proteins and Reduced Release of Cytochrome c", *Experimental Cell Research*, 235 (1), Article No. EX973667,(1997), 210–217.

Wechter, W. J., et al., "E–7869 (R–Flurbiprofen) Inhibits Progression of Prostate Cancer in the TRAMP Mouse", *Cancer Research*, 60, (Apr. 15, 2000), 2203–2208.

Weiss, H. A., et al., "Aspirin, Non–Steroidal Anti–Inflammatory Drugs and Protection from Colorectal Cancer: a Review of the Epidemiological Evidence", *Scandinavian Journal of Gastroenterology*, 31 (Suppl. 220), (1996), 137–141.

Wilen, S. H., et al., "Strategies in Optical Resolutions", *Tetrahedron*, 33 (21), Tetrahedron Report No. 38,(1977), 2725–2736.

*The Merck Index, Thirteenth Edition*, Badavari, S., et al., (eds.), Merck & Co., Inc., Rahway, N.J., "Etodolac, Entry No. 3905",(1990),p. 685.

*In: Remington's Pharmaceutical Sciences, Eighteenth Edition*, Gennaro, A.R., (ed.), Mack Publishing Company, Easton, PA,(1990),pp. 1115–1122.

Heath, Clark W., "Nonsteroidal Antiinflammatory Drugs and Human Cancer", *American Cancer Society*, vol. 74, No. 10, (Nov. 15, 1994),2885–2886.

McCracken, John D., "Antiproliferative Effects of the Enantiomers of Flurbiprofen", *Journal of Clinical Pharmacology*, (1996), 540–545.

Piazza, Gary A., "Apoptois Primarily Accounts for the Growth–inhibitory Properties of Sulindac Metabolites and Involves a Mechanism That is Independent of Cyclooxygebase Inhibition, Cell Cycles Arrest, and p53 Induction", *Cancer Research*, vol. 57, (Jun. 15, 1997),2452–2459.

Riley, et al., "New Drugs: a six month review", *US Pharamacist*, vol. 16, (Sep. 1991),35–64.

Thun, Michael J., "Aspirin, NSAIDs, and digestive tract cancers", *Cancer and Metastasis Reviews 13, Kluwer Academic Publishers.*, (1994),269–277.

Wechter, William J., "R–Flubiprofen (E–7869), a chemopreventive and treatment of cancer", *Inflammopharmacology*, vol. 8, No. 2, (2000), 189–206.

Wechter, William J., "R–Flurbiprofen Chemoprevention and Treatment of Intestinal Adenomas in the APC min/+ Mouse Model: Implications for Prophylaxis and Treartment of Colon Cancer", *Cancer Research*, vol. 57, No. 19, (Oct. 1, 1997),4316–4324.

Wechter, William J., "Rac–Flurbiprofen is More Ulcerogenic Than Its (S)–Enantiomer", *Chirality*, vol. 5, No. 7, (1993),492–494.

Mycek, M. J., et al., "Anticancer Drugs", *Lippincott's Illustrated Reviews: Pharmacology, Second Edition,* (1997),373; 387–395.

*Drug Facts and Comparsions, 1995 Edition,* Wolters Kluwer Co., (1995),2775–2789.

* cited by examiner

USE OF ETODOLAC TO TREAT HYPERPLASIA

CROSS-REFERENCE TO RELATED APPLICATIONS

This application claims priority of U.S. provisional patent application Ser. No. 60/412,193, filed Sep. 19, 2002, which is incorporated by reference herein.

GOVERNMENT FUNDING

This invention was made with the assistance of the National Institutes of Health under Grant Nos. AR47360 and GM23200. The U.S. Government has certain rights in this invention.

BACKGROUND OF THE INVENTION

Hyperplastic diseases are non-malignant conditions that represent an unmet medical need. Typically, these diseases are characterized by the uncontrolled growth of cells. In many patients these cells are not malignant and the hyperplastic cells do not lead to the development of cancer. Thus, the hyperplastic cells are not treated with the conventional chemotherapeutic agents useful against malignant diseases.

One example of a hyperplastic disease is benign prostatic hypertrophy (BPH). This disease is characterized by the abnormal growth of the prostate. Substantial data currently exist showing that prostate volume increases with age in a measurable group of middle-aged and older men, following a post-pubertal plateau. In addition, the incidence and prevalence of prostate disease increase with age, and are very high in elderly men (>40%). Other non-malignant hyperplastic diseases include, but are not limited to fibroplastic dysplasia of the breast, fibroplastic growths in the uterus or cervix, and gastric hyperplastic polyposis. In many patients, hyperplastic diseases do not lead to the development of cancer, and are not treated with the conventional chemotherapeutic agents used against malignant diseases.

Therefore, a continuing need exists for new, potent, and selective agents useful to prevent detrimental effects or control the growth of hyperplastic cells.

SUMMARY OF THE INVENTION

In one aspect, the present invention provides a therapeutic method to treat non-malignant diseases characterized by the excessive tissue growth, e.g., hyperplastic diseases, comprising administering to a mammal (e.g., human) afflicted with excessive tissue growth, an effective amount of a derivative of an indole compound of formula (I):

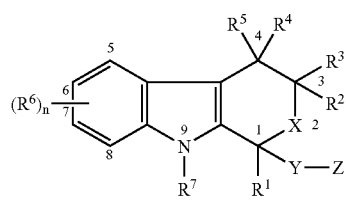

I wherein $R^1$ is lower alkyl, (hydroxy)lower alkyl, lower alkenyl, lower alkynyl, lower cycloalkyl, phenyl, benzyl or 2-thienyl;

$R^2$, $R^3$, $R^4$ and $R^5$ are the same or different and are each hydrogen or lower alkyl;

each $R^6$ is independently hydrogen, lower alkyl, hydroxy, (hydroxy)lower alkyl, lower alkoxy, benzyloxy, lower alkanoyloxy, nitro or halo;

$R^7$ is hydrogen, lower alkyl or lower alkenyl, X is oxy and thio, Y is carbonyl, —($C_1$–$C_3$)alkyl(CO)—, —($CH_2$)$_{1-3}$—, or —($CH_2$)$_{1-3}$$SO_2$—;

Z is hydroxy, lower alkoxy, ($C_2$–$C_4$)acyloxy, —N($R^8$)($R^9$), phenylamino, (ω-(4-pyridyl)($C_2$–$C_4$ alkoxy), (ω-(($R^8$)($R^9$) amino)($C_2$–$C_4$ alkoxy), an amino acid ester of (ω-(HO)($C_2$–$C_4$))alkoxy, —N($R^8$)CH($R^8$)$CO_2$H, 1'-D-glucuronyloxy, —$SO_3$H, —$PO_4H_2$, —N(NO)(OH), —$SO_2NH_2$, —PO(OH)($NH_2$), —$OCH_2CH_2$N($CH_3$)$_3^+$, or tetrazolyl;

wherein $R^8$ and $R^9$ are each H, ($C_1$–$C_3$)alkyl or together with N are a 5- or 6-membered heterocyclic ring comprising 1–3 —N($R^8$)—, S or nonperoxide O; n is 1–3; and each alkyl or phenyl group of $R^1$, $R^2$, $R^3$, $R^4$, $R^5$, $R^6$, $R^7$ and Z is optionally substituted with 1, 2, or 3 ($C_1$–$C_4$) alkyl groups; or a pharmaceutically acceptable salt thereof.

In addition, the invention includes a therapeutic method for treatment of mammalian hyperplastic cells comprising administering to a patient in need of said therapy a chemotherapeutic agent in combination with an effective amount of a compound of formula (I).

In another embodiment, the compound of formula (I) is etodolac, R(-)-etodolac, or an analog thereof, effective to inhibit or control the growth of the hyperplastic cells of said mammal. The viability of the hyperplastic cells is reduced selectively, while maintaining the viability of normal cells.

Thus, the invention provides a therapeutic method for the treatment of a human or other mammal afflicted with a hyperplastic disease such as, for example, benign prostate hyperplasia (BPH), fibroplastic dysplasia of the breast, fibroplastic growth in the uterus or fibroplastic growth in the cervix wherein an effective amount of etodolac or an analog thereof is administered to an afflicted subject undergoing treatment with one or more chemotherapeutic agents, wherein the hyperplastic cells are rendered more susceptible to the chemotherapeutic agent(s).

The present invention also provides a method of increasing the susceptibility of human hyperplastic cells to a chemotherapeutic agent comprising contacting the cells with an effective sensitizing amount of a compound of formula (I), e.g., etodolac, or an analog thereof.

Further it is applicants' belief that the present invention can provide a synergistic effect when an effective amount of a compound of formula (I), e.g., etodolac, or an analog thereof is administered in combination with a chemotherapeutic agent.

In one aspect, the compounds of formula (I) are administered in conjunction with one or more chemotherapeutic agents effective against BPH, fibroplastic dysplasia of the breast, fibroplastic growths in the uterus or cervix, and gastric hyperplastic polyposis. Examples of chemotherapeutic agents include androgen inhibitors, such as, for example, finasteride, and the like; α-1 adrenergic receptor blockers such as, for example, phenoxybenzamine, prozosin, terazin, doxazosin, tamsulosin, and the like. Thus, the compound of formula (I) can be used alone, or preferably, in combination with a chemotherapeutic agent.

The invention also provides a compound of formula I for use in medical therapy (preferably for use in treating hyperplastic diseases as well as the use of a compound of formula I for the manufacture of a medicament for the treatment of a pathological condition or symptom in a mammal, such as a human, which is associated with hyperplastic diseases.

The present invention is based on the discovery by the inventors that a compound of formula (I), such as, for example, R-etodolac reduces the overall size of the prostates of mice treated with these compounds. The treated mice were found to have prostates that had a reduction of the overall size of the prostates when compared to untreated mice.

DETAILED DESCRIPTION OF THE INVENTION

The compounds useful in the methods of the invention include a compound of formula (I):

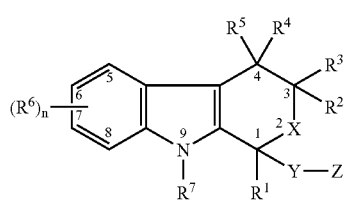

wherein $R^1$ is lower alkyl, (hydroxy)lower alkyl, lower alkenyl, lower alkynyl, lower cycloalkyl, phenyl, benzyl or 2-thienyl; $R^2$, $R^3$, $R^4$ and $R^5$ are the same or different and are each hydrogen or lower alkyl; each $R^6$ is individually hydrogen, lower alkyl, hydroxy, (hydroxy)lower alkyl, lower alkoxy, benzyloxy, lower alkanoyloxy, nitro or halo, $R^7$ is hydrogen, lower alkyl or lower alkenyl, X is oxy and thio, Y is carbonyl, $—(CH_2)_{1-3}—$, $—(C_1-C_3)alkyl(CO)—$, or $—(CH_2)_{1-3}SO_2—$; Z is hydroxy, lower alkoxy, $(C_2–C_4)$ acyloxy, $—N(R^8)(R^9)$, phenylamino, (ω-(4-pyridyl)($C_2–C_4$ alkoxy), (ω-(($R^8$)($R^9$) amino)($C_2–C_4$ alkoxy), an amino acid ester of (ω-(HO)($C_2–C_4$))alkoxy, $—N(R^8)CH(R^8)CO_2H$, 1'-D-glucuronyloxy, $—SO_3H$, $—PO_4H_2$, $—N(NO)(OH)$, $—SO_2NH_2$, $—PO(OH)(NH_2)$, $—OCH_2CH_2N(CH_3)_3^+$, or tetrazolyl; wherein $R^8$ and $R^9$ are each H, $(C_1–C_3)$alkyl or together with N are a 5- or 6-membered heterocyclic ring comprising 1–3 $N(R^8)$, S or nonperoxide O; n is 0, 1, 2, or 3; wherein $R^8$ and $R^9$ are each H, $(C_1–C_3)$alkyl or together with N are a 5- or 6-membered heterocyclic ring comprising 1–3 $N(R^8)$, S or nonperoxide O; each alkyl or phenyl group of $R^1$, $R^2$, $R^3$, $R^4$, $R^5$, $R^6$, $R^7$ and Z is optionally substituted with 1, 2, or 3 $(C_1–C_4)$alkyl groups; or a pharmaceutically acceptable salt thereof.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

As used herein, with respect to hyperplasia, the term "inhibition" or "inhibit" includes both the reduction in cellular proliferation, blockage of cellular proliferation, or killing some or all of the hyperplastic cells. Thus, the term can be used in both the context of a prophylactic treatment to prevent development of hyperplasia or as a treatment that will block, or slow the growth of hyperplastic cells.

As used herein "treating" includes (i) preventing a pathologic condition from occurring (e.g., prophylaxis) or symptoms related to the same; (ii) inhibiting the pathologic condition or arresting its development or symptoms related to the same; and (iii) relieving the pathologic condition or symptoms related to the same.

As used herein "in combination with" or "administered in conjunction with" includes simultaneous administration, separate administration or sequential administration of the active agents in a manner that allows the beneficial effect desired to occur.

As used herein, an "analog of etodolac" includes the compounds of formula (I) and pharmaceutically acceptable salts thereof.

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, lower alkyl refers to $(C_1–C_6)$alkyl and includes methyl, ethyl, propyl, isopropyl, butyl, iso-butyl, sec-butyl, pentyl, 3-pentyl, or hexyl; $(C_3–C_6)$cycloalkyl includes cyclopropyl, cyclobutyl, cyclopentyl, or cyclohexyl; lower alkoxy refers to $(C_1–C_6)$alkoxy and includes methoxy, ethoxy, propoxy, isopropoxy, butoxy, iso-butoxy, sec-butoxy, pentoxy, 3-pentoxy, or hexyloxy; lower alkenyl refers to $(C_1–C_6)$alkenyl and includes vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; lower alkynyl refers to $(C_1–C_6)$alkynyl and includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; (hydroxy) lower alkyl refers to (hydroxy)$(C_1–C_6)$alkyl and includes hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; lower alkanoyloxy refers to $(C_2–C_6)$alkanoyloxy and includes acetoxy, propanoyloxy, butanoyloxy, isobutanoyloxy, pentanoyloxy, or hexanoyloxy.

The term "amino acid," comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, omithine, citruline, -methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a $(C_1–C_6)$alkyl, phenyl or benzyl ester or amide; or as an -methylbenzyl amide). Other suitable amino and carboxy protecting groups are known to those skilled in the art (See for example, T. W. Greene, *Protecting Groups In Organic Synthesis;* Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

A specific value for $R^1$ is hydrogen or lower alkyl.
A more specific value for $R^1$ is ethyl.
A specific value for $R^2$ is hydrogen.
A specific value for $R^3$ is hydrogen.
A specific value for $R^4$ is hydrogen.
A specific value for $R^5$ is hydrogen.
A specific value for $R^6$ is hydrogen or alkyl.
A more specific value for $R^6$ is hydrogen.
A more specific value for $R^6$ is ethyl.

A specific value for n is 1.
A specific value for $R^7$ is hydrogen.
A specific value for Y is —$(CH_2)_{1-3}C(O)$.
A more specific value for Y is —$(CH_2)C(O)$.
A specific value for Z is OH., $OCH_2CH_2N(CH_3)_3^+$, N-morpholinoethoxy, L-valine ester of 2-hydroxyethoxy or L-glycine ester of 2-hydroxyethoxy.
A more specific value for Z is OH
A more specific value for Z is $OCH_2CH_2N(CH_3)_3^+$
A more specific value for Z is N-morpholinoethoxy.
A more specific value for Z is the L-valine ester of 2-hydroxyethoxy or L-glycine ester of 2-hydroxyethoxy.
A specific value for X is oxy.
Specific compounds of the invention are the R(−) isomer of the compounds having formula (I).
A specific compound of the invention, Etodolac (1,8-diethyl-1,3,4,9-tetrahydro[3,4-6]indole-1-acetic acid) is a NSAID of the pyranocarboxylic acid class that was developed in the early 1970s. See, C. A. Demerson et al., Ger. Pat. No. 2,226,340 (Am. Home Products); C. A. Demerson, et al. U.S. Pat. No. 3,843,681; R. R. Martel et al., Can. J. Pharmacol., 54, 245 (1976). Its structure is depicted as formula (II), below, wherein (*) denotes the chiral center. See also, The Merck Index, (11th ed.), at page 608.

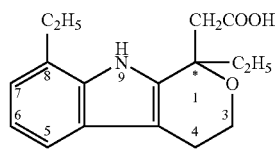

II

The pharmacokinetics of etodolac have been extensively reviewed by D. R. Brocks et al., Clin. Pharmacokinet., 26, 259 (1994). Etodolac is marketed as the racemate. The absolute configurations of the enantiomers were found to be S-(+) and R-(−), which is similar to that for most other NSAIDs. However, Demerson et al., J. Med. Chem., 26, 1778 (1983) found that the S(+)-enantiomer of etodolac possessed almost all of the anti-inflammatory activity of the racemate, as measured by reduction in paw volume of rats with adjuvant polyarthritis, and prostaglandin synthetase inhibitory activity of the drug. No anti-inflammatory activity was discernible with the R(−)-enantiomer, and it is not converted significantly to the S(+) enantiomer in vivo. Hence, R(−) etodolac is not a NSAID. However, as disclosed below, R(−) etodolac paradoxically was found to have potent activity against hyperplastic cells that is at least equivalent to that of the S(+) enantiomer.

Etodolac possesses several unique disposition features due to their stereoselective pharmacokinetics. In plasma, after the administration of RS-etodolac, the concentrations of the "inactive" R-enantiomer of etodolac are about 10-fold higher than those of the active S-enantiomer, an observation that is novel among the chiral NSAIDs. See, D. R. Brocks et al., Clin. Pharmacokinet., 26, 259 (1994). After a 200 mg dose in six elderly patients, the maximum plasma concentration of the R-enantiomer was about 33 μM. In contrast, the maximum concentration of the S-enantiomer was 5-fold lower. The typical dosage of the racemic mixture of etodolac is 400 mg BID, and the drug has an elimination half-life between 6–8 hours. Moreover, it is believed that the administration of the R-enantiomer alone will not display the side effects associated with cyclooxygenase (COX) inhibitors, such as ulcers and renal insufficiency, and thus can be given at considerably higher dosages. In addition, the compounds of formula (I) can be dissolved in water and other aqueous carriers at substantially high concentrations.

Compounds of the invention can be prepared as disclosed in U.S. Pat. No. 3,843,681, U.S. patent application Ser. No. 09/313,048, Ger. Pat. No. 2,226,340 (Amer. Home Products), R. R. Martel et al., Can. J. Pharmacol., 54, 245 (1976); Demerson et al., J. Med. Chem., 19, 391 (1976); PCT application Ser. No. US/01/24978, and Rubin (U.S. Pat. No. 4,337,760).

The resolution of racemic compounds of formula (I) can be accomplished using conventional means, such as the formation of a diastereomeric salt with a optically active resolving amine; see, for example, "Stereochemistry of Carbon Compounds," by E. L. Eliel (McGraw Hill, 1962); C. H. Lochmuller et al., J Chromatog., 113, 283 (1975); "Enantiomers, Racemates and Resolutions," by J. Jacques, A. Collet, and S. H. Wilen, (Wiley-Interscience, New York, 1981); and S. H. Wilen, A. Collet, and J. Jacques, Tetrahedron, 33, 2725 (1977). For example, the racemates of etodolac has been resolved by fractional crystallization of RS-etodolac using optically active 1-phenylethylamine. HPLC has been used to determine racemic etodolac and enantiomeric ratios of etodolac and two hydroxylated metabolites in urine (U. Becker-Scharfenkamp et al., J. Chromatog., 621, 199 (1993)). B. M. Adger et al. (U.S. Pat. No. 5,811,558), disclosed the resolution of etodolac using glutamine and N($C_1$–$C_4$ alkyl)-glutamine salts.

The magnitude of a prophylactic or therapeutic dose of racemic or R-etodolac in the treatment of a hyperplastic disease, i.e., BPH, will vary with the progression of the disease, such as the location of the growth to be treated, the chemotherapeutic agent(s) or other therapy used, and the route of administration. The dose, and perhaps the dose frequency, will also vary according to the age, body weight, and response of the individual patient. In general, the total daily dose range for racemic or R-etodolac, for the conditions described herein, is from about 50 mg to about 5000 mg, in single or divided doses. Preferably, a daily dose range should be about 100 mg to about 4000 mg, most preferably about 1000–3000 mg, in single or divided doses, e.g., 750 mg every 6 hr of orally administered R(−)-etodolac. This can achieve plasma levels of about 500–750 μM, which was shown to reduce the size of the prostate in the animal models. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

The compounds of formula (I) can also be prepared in the form of their pharmaceutically acceptable salts or their non-pharmaceutically acceptable salts. The non-pharmaceutically acceptable salts are useful as intermediates for the preparation of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. Preferred carboxylic acid salts are those of hydrophilic amines, such as glucamine or N—($C_1$–$C_4$) alkylglucamine (see, Adger et al. (U.S. Pat. No. 5,811,558)).

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any suitable route of administration may be employed for providing the patient with an effective dosage of etodolac, i.e., R(−)etodolac. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The etodolac may be administered prior to, concurrently with, or after administration of chemotherapy, or continuously, i.e., in daily doses, during all or part of, a chemotherapy regimen, such as, for example, treatment with an androgen, or α-1 adrenergic receptor blockers. The etodolac, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrated agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, such as, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, such as, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known in the art; for example, see U.S. Pat. No. 4,938,949.

The invention will be further described by reference to the following detailed example.

EXAMPLE 1

TRAMP Animal Model

The transgenic adenocarcinoma mouse prostate (TRAMP) mouse, was used to evaluate the effect of R-etodolac on prostate cancer progression. The etodolac was compounded into the diet at 312 ppm (low dose) and 1250 ppm (high dose) and the animals were treated for 18 weeks. At necoscopy, the urogenital system was removed and weighed. The prostate lobes, seminal vesicles, lungs, liver, and periaortic lymph nodes were preserved and sectioned for histological evaluation and graded on a 1–6 scale for degree of hyperplasia/neoplasia/carcinoma.

TABLE 1

Table 1. Average weight of dissected prostate lobes. Weights are given as average ± standard deviation

| Average weigh (g) | Control | Low Dose | High Dose |
|---|---|---|---|
| Anterior Prostate | 0.095 ± .052 | 0.062 ± 0.033 | 0.076 ± 0.012 |
| Ventral prostate | 0.023 ± .009 | 0.024 ± 0.017 | 0.014 ± 0.001 |
| Lateral Prostate | 0.026 ± 0.11 | 0.015 ± 0.001 | 0.016 ± 0.003 |
| Dorsal Prostate | 0.169 ± 0.167 | 0.062 ± 0.027 | 0.053 ± 0.013 |
| Total Weigh average | 3.261 ± 4.9 | 1.804 ± 2.38 | 0.160 ± 0.022 |

TABLE 2

Table 2. Histopathological evaluation of the prostate in TRAMP mice treated with R-etodolac.

| Number | Group | Anterior | Dorsal | Lateral | Ventral | Average mouse Staging | Overall Mean |
|---|---|---|---|---|---|---|---|
| 19 | Control | 5 | 5 | 5 | 5 | 5.0 | 4.7 |
| 46 | Control | 4 | 6 | 5 | 5 | 5.0 | |
| 86 | Control | 6 | 6 | 6 | 6 | 6.0 | |
| 88 | Control | 4 | 5 | 4 | 3 | 4.0 | |
| 90 | Control | 4 | 6 | 6 | 3 | 4.8 | |
| 91 | Control | n.a. | 4 | 4 | 3 | 4.3 | |
| 101 | Control | 3 | 5 | 3 | 4 | 3.8 | |
| 78 | Low dose | 3 | 4 | 3 | 6 | 4.0 | 4.3 |
| 79 | Low dose | 4 | 6 | 6 | 6 | 5.5 | |
| 81 | Low dose | 4 | 5 | 4 | 3 | 4.0 | |
| 85 | Low dose | 4 | 4 | 3.5 | 3 | 3.6 | |
| 95 | Low dose | 4 | 5 | 5 | 4 | 4.5 | |
| 96 | Low dose | 6 | 6 | 6 | 6 | 6.0 | |
| 25 | High dose | 3 | 4 | 4 | 4 | 3.8 | 3.3* |
| 27 | High dose | 4 | 4 | 3 | 2 | 3.3 | |
| 30 | High dose | 3 | 4 | 3 | 3 | 3.3 | |
| 41 | High dose | 3 | 4 | 3 | 3 | 3.3 | |
| 72 | High dose | 3 | 4 | 4 | 3 | 3.5 | |
| 75 | High dose | 3 | 3 | 3 | 3 | 3.0 | |

*statistically significant from control group, p < 0.005, Mann Whitney t test

TABLE 3

Table 3: Definition of the histopathological grades for the TRAMP model.

| Grade | Definition | Description |
|---|---|---|
| 1 | Normal Prostate | In the normal prostate, epithelial cells comprising the glands are uniform in size and orientation, and their nuclei are small and well-defined. |
| 2 | Early intra-epithelial neoplasia | Early neoplastic changes are evident as an increase in epithelial nuclear-to-cytoplasmic ratio and "tufting up" of the epithelial layer or layers into the glandular lumen. This lesion is analogous to a low grade PIN lesion in humans. |
| 3 | Advanced intra-epithelial neoplasia | This lesion is analogous to a more-advanced PIN lesion in humans and is associated with extensive infolding of epithelial cell layers into the lumen and an increase in both mitotic and/or apoptotic figures. |
| 4 | Well-differentiated adeno-carcinoma | This grade of cancer is represented by early invasion/penetration of the glandular basement membrane by tumor cells that extend into the stromal compartment. |
| 5 | Moderately differentiated adeno-carcinoma | Moderately-differentiated cancer is represented by tumor formation of primitive glands lacking an obvious lumen. Tumor cells comprising these glands have lost their tall secretory appearance. |
| 6 | Poorly differentiated adeno-carcinoma | This most severe grade of prostate cancer is represented by tumors composed of sheets and cords of highly pleiomorphic anaplastic tumor cells. |

It was found that for the TRAMP mice treated with R-etodolac at the highest dose there was a reduction of the overall size of the prostates (Table 1). In addition, histological analysis demonstrated that R-etodolac was able to affect the progression of the disease, maintaining the animals in a pre-cancerous stage characterized by a low amount of mitotic events and reduced levels of morphological alterations (Table 2). The inhibition of the prostate enlargement may be due to the specific inhibition of proliferation of cells that are not yet neoplastic, but only hyperplastic. No other effects in any other tissues were observed in the TRAMP mice treated with R-etodolac.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A therapeutic method for treatment of non-malignant diseases characterized by the excessive growth of tissue comprising administering to a patient in need of said therapy, an effective amount of a compound of formula (I):

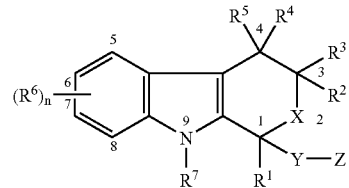

wherein $R^1$ is lower alkyl, (hydroxy)lower alkyl, lower alkenyl, lower alkynyl, lower cycloalkyl, phenyl, benzyl or 2-thienyl;

$R^2$, $R^3$, $R^4$ and $R^5$ are the same or different and are each hydrogen or lower alkyl;

each $R^6$ is independently hydrogen, lower alkyl, hydroxy, (hydroxy)lower alkyl, lower alkoxy, benzyloxy, lower alkanoyloxy, nitro or halo;

$R^7$ is hydrogen, lower alkyl or lower alkenyl, X is oxy or thio, Y is carbonyl, $-(C_1-C_3)$alkyl(CO)$-$, $-(CH_2)_{1-3}-$, or $-(CH_2)_{1-3}SO_2-$;

Z is hydroxy, lower alkoxy, $(C_2-C_4)$acyloxy, $-N(R^8)(R^9)$, phenylamino, ($\omega$-(4-pyridyl)($C_2-C_4$ alkoxy), ($\omega$-

$((R^8)(R^9)$ amino)$(C_2-C_4$ alkoxy), an amino acid ester of $(\omega\text{-}(HO)(C_2-C_4))$alkoxy, —$N(R^8)CH(R^8)CO_2H$, 1'-D-glucuronyloxy, —$SO_3H$, —$PO_4H_2$, —$N(NO)(OH)$, —$SO_2NH_2$, —$PO(OH)(NH_2)$, —$OCH_2CH_2N(CH_3)_3^+$, or tetrazolyl;

wherein $R^8$ and $R^9$ are each H, $(C_1-C_3)$alkyl or together with N are a 5- or 6-membered heterocyclic ring comprising 1–3 $N(R^8)$, S or nonperoxide O; n is 0, 1, 2, or 3; and each alkyl or phenyl group of $R^1$, $R^2$, $R^3$, $R^4$, $R^5$, $R^6$, $R^7$ and Z is optionally substituted with 1, 2, or 3 $(C_1-C_4)$alkyl groups; or a pharmaceutically acceptable salt thereof;

wherein the disease is benign prostate hyperplasia.

2. The method of claim 1, wherein the compound of formula (I) is administered orally.

3. The method of claim 1, wherein the compound of formula (I) is administered in combination with an androgen inhibitor, or an α-1 adrenergic receptor blocker.

4. The method of claim 3, wherein the androgen inhibitor is finasteride.

5. The method of claim 3, wherein the α-1 adrenergic receptor blocker is phenoxybenzamine, prazosin, terazin, doxazosin, or tamsulosin.

6. The method of claim 1, wherein Z is the L-valine or L-glycine ester of 2-hydroxyethoxy.

7. The method of claim 1, wherein Z is N-morpholinoethoxy.

8. The method of claim 1, wherein each $R^8$ is H, $CH_3$ or i-Pr.

9. The method of claim 1, wherein Z is $OCH_2CH_2N(CH_3)_3$.

10. The method of claim 1, wherein the compound of formula (I) is etodolac.

11. The method of claim 1, wherein the compound of formula (I) is the R(−)isomer.

* * * * *

UNITED STATES PATENT AND TRADEMARK OFFICE
CERTIFICATE OF CORRECTION

PATENT NO.      : 7,211,599 B2
APPLICATION NO. : 10/667208
DATED           : May 1, 2007
INVENTOR(S)     : Carson et al.

It is certified that error appears in the above-identified patent and that said Letters Patent is hereby corrected as shown below:

On the title page, item (56), under "Other Publications", in column 2, line 2, delete "Antiimflammatory" and insert -- Antiinflammatory --, therefor.

On page 2, item (56), under "U.S. Patent Documents", in column 1, line 30, below "5,968,974 A" insert -- 5,981,592  11/1999  Wechter et al.  514/570 --.

On page 2, item (56), under "U.S. Patent Documents", in column 1, line 36, below "6,552,055 B1" insert -- 2002/0042375A1  4/2002  Heimbrook et al.  514/16 --.

On page 2, item (56), under "Other Publications", in column 1, line 10, after "B.," insert -- et al., --.

On page 3, in item (56), under "Other Publications", in column 1, line 7, delete "b" and insert -- B --, therefor.

On page 3, item (56), under "Other Publications", in column 2, line 4, delete "Badavari," and insert -- Budavari, --, therefor.

On page 3, item (56), under "Other Publications", in column 2, line 26, delete "Flubiprofen" and insert -- Flurbiprofen --, therefor.

On page 3, item (56), under "Other Publications", in column 2, line 40, delete "Comparsions," and insert -- Comparisons, --, therefor.

In column 4, line 42, delete "omithine," and insert -- ornithine, --, therefor.

UNITED STATES PATENT AND TRADEMARK OFFICE
CERTIFICATE OF CORRECTION

PATENT NO. : 7,211,599 B2
APPLICATION NO. : 10/667208
DATED : May 1, 2007
INVENTOR(S) : Carson et al.

It is certified that error appears in the above-identified patent and that said Letters Patent is hereby corrected as shown below:

In column 5, line 9, after "$(CH_3)_3^+$" insert -- . --.

Signed and Sealed this

Twenty-ninth Day of December, 2009

David J. Kappos
*Director of the United States Patent and Trademark Office*